(12) United States Patent
Kebart et al.

(10) Patent No.: US 6,802,214 B2
(45) Date of Patent: Oct. 12, 2004

(54) ENVELOPE QUALITY CONTROL APPARATUS

(75) Inventors: Brian Kebart, Branchburg, NJ (US);
Jeffrey Reed, Newport News, VA (US);
George Pesansky, Walnutport, PA (US);
Preston Burton, Newport News, VA (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 24 days.

(21) Appl. No.: 10/364,795

(22) Filed: Feb. 11, 2003

(65) Prior Publication Data

US 2004/0154415 A1 Aug. 12, 2004

(51) Int. Cl.[7] .............................. G01N 3/10; G01B 3/18; G01B 5/06
(52) U.S. Cl. .................. 73/150 A; 33/553; 33/813; 73/827; 73/834; 493/37
(58) Field of Search .................... 33/551, 553–554, 33/813; 73/52, 150 A, 150 R, 827, 834, 860; 156/64; 493/6, 37

(56) References Cited

U.S. PATENT DOCUMENTS

| | | | | |
|---|---|---|---|---|
| 3,246,513 A | * | 4/1966 | Morris | 73/150 R |
| 3,678,738 A | * | 7/1972 | Jubelt | 73/827 |
| 4,679,444 A | * | 7/1987 | Kiefer | 73/827 |
| 4,862,740 A | * | 9/1989 | Lanier | 73/150 A |
| 5,111,701 A | * | 5/1992 | Klein | 73/827 |
| 5,276,974 A | * | 1/1994 | Chanoni et al. | 33/503 |
| 6,212,786 B1 | * | 4/2001 | Naoi | 33/573 |
| 6,367,159 B1 | * | 4/2002 | Naoi et al. | 33/552 |
| 6,378,221 B1 | * | 4/2002 | Ekholm et al. | 33/551 |
| 6,711,828 B2 | * | 3/2004 | McCune et al. | 33/533 |

\* cited by examiner

*Primary Examiner*—Hezron Williams
*Assistant Examiner*—John Hanley
(74) *Attorney, Agent, or Firm*—Charles W. Almer

(57) ABSTRACT

A unit for evaluating various properties of a paper envelope. The unit is capable of examining an envelope and determining key features of the envelope, such as the amount of front seal adhesive present, the tear strength of the side seams and the presence of properly printed graphics. The unit comprises a) a housing having either a touch screen video display unit or another source of data entry; b) a front seal control portion that contains linear encoders to determine the amount of adhesive on the seal; c) a side strength control portion that contains blades used to measure the force needed to burst the sides of the envelope: and d) a print design quality feature that is utilized to confirm the quality and location of any printing on the envelope.

11 Claims, 3 Drawing Sheets

ENVELOPE QUALITY CONTROL APPARATUS

FIELD OF THE INVENTION

The present invention relates to an apparatus for testing various properties of envelopes.

BACKGROUND OF THE INVENTION

The envelope manufacturing industry involves the production of an extremely large number of units at a very high-speed production rate and a minimal material cost per unit. During envelope production, several key criteria, such as the consistency of the application of adhesive along the front seal and the strength of the bond along the side and back seams, are critical to the manufacture of an acceptable envelope. The industry is continuously striving to maximize the output of units and minimize return and waste units, many of which are caused by failures in the above key criteria. The industry's profits and sales are based upon the minimization of failures in the envelopes.

A number of obstacles have arisen in recent years which have resulted in decreased sales and profits for the industry. One cause is the increase in alternative means of communication, such as the Internet, that do not require the use of envelopes. Further, the tragic events of Sep. 11, 2001 and subsequent anthrax scare have placed an increased focus on safety and security within the industry. A separate issue has been created by the increased use of recycled paper in that such recycled paper does not always bond as neatly as non-recycled paper.

Accordingly, the envelope manufacturing industry is in need of a system for inspecting envelopes in order to ensure that envelopes are structurally sound before they are shipped to customers. It would be advantageous if such a system could inspect key features of the envelope, such as the consistency of the adhesive along the front seal and the strength of the bond along the side and back seams. Such a system would provide distinct competitive and economic advantages to an envelope manufacturer.

SUMMARY OF THE INVENTION

The present invention discloses a unit for evaluating various properties of a paper envelope. The unit is capable of examining an envelope and determining key features of the envelope, such as the amount of front seal adhesive present, the tear strength of the side seams and the presence of properly printed graphics. The unit comprises a) a housing having either a touch screen video display unit or another source df data entry; b) a front seal control portion that contains linear encoders to determine the amount of adhesive on the seal; c) a side strength control portion that contains blades used to measure the force needed to burst the sides of the envelope; and d) a print design quality feature that is utilized to confirm the quality and location of any printing on the envelope.

DETAILED DESCRIPTION OF THE PREFERRED EMBODIMENTS

The envelope testing system of the present invention comprises a modular unit to which various testing devices may be incorporated. These testing devices perform tests on paper envelopes that previously were required to be manually performed. While what will be described herein are many of the testing features that may be incorporated, it is to be understood that the system may comprise additional, or fewer, testing features than those set out in this application. The main purpose of the testing is three-fold: 1) to enable envelope manufacturers to streamline their quality control processes; 2) to automatically collect data regarding the envelopes that is not available without the use of the system; and 3) to eliminate the subjectivity that is often inherent in quality control procedures. The first purpose, streamline the quality control processes involves the systematical testing of the envelope's adhesive thickness on the left, center and right sides of the front seal, testing the strength of the side or back seam adhesive and visually inspecting the envelope for graphics content and quality. The data collection function allows envelope manufacturers to acquire and compare data from various production and line runs. An advantage of this data collection capability is that it facilitates quality control measures based on long term data trends.

Figure 1:
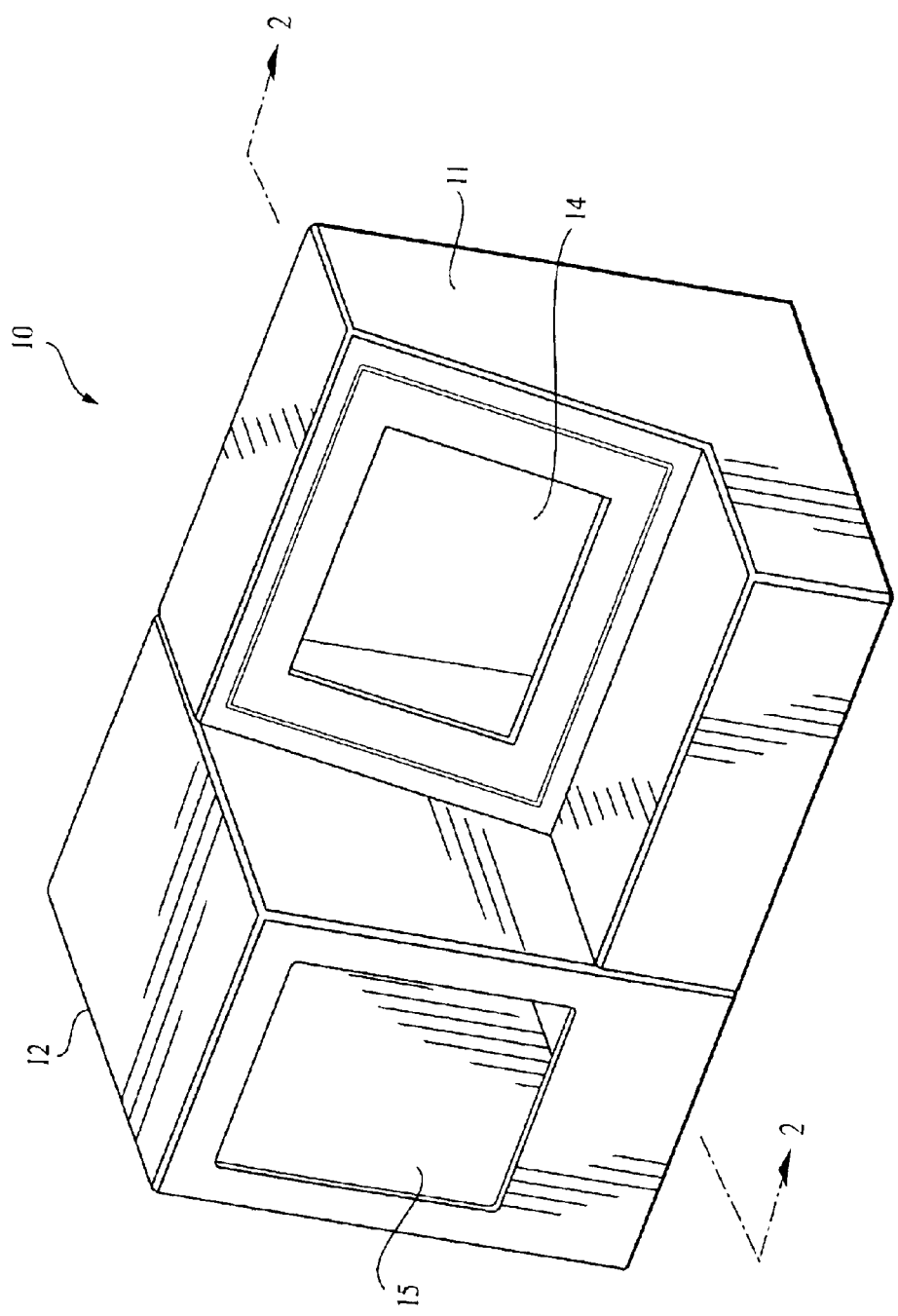
FIG. 1 is a perspective view of the housing of the envelope testing unit.
Figure 2:
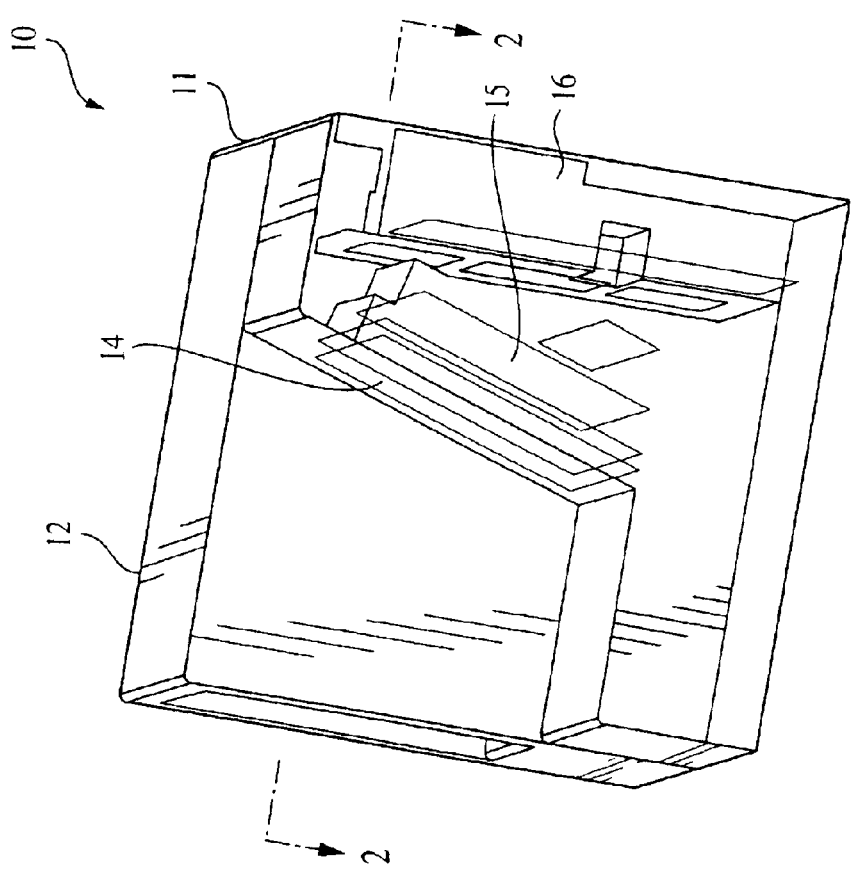
FIG. 2 is a cut-away view of the housing of the envelope testing unit.

FIG. 1 illustrates the first component of the testing system. Housing 10 comprises a first section 11 having a user interface and computer systems and a second section 12 that contains the envelope testing devices. Section 11 contains an area 14 that acts as the user interface for transmitting test requests and receiving test data. The user interface is preferably in the form of a touch screen visual video display unit. The video display unit is interactive such that the user may set any desired testing parameters and also receive data feedback. As shown in FIG. 2, the backside of the video display unit contains a central processing unit in the form of a computer and electronic equipment 15, 16 sufficient to control and monitor the testing. Preferably, the computer 15 is an IBM PC computer with LCD touch screen human-machine interface (HMI). The computer must be capable of supporting custom C++ software modules that will form the controlling strategy for the system. The computer must also be capable of interfacing with various electronic subsystems.

Power is introduced into the system via a standard fused socket that typically may be located on the back of the housing. A servo motor controlled printed circuit board 16 accepts the incoming power supply which is preferably in the dual form of a 12 volt DC control power supply and a 36 volt motor drive power supply (not illustrated). A communication port connects the printed circuit board with the computer such that command impetus is transmitted from the computer to the printed circuit board, while motor, I/O and board status is returned to the computer. The printed circuit board contains a series of microcontrollers that provide velocity and position control over each of the linear motion drives required for testing the envelopes. The printed circuit board preferably features analog to digital conversion with 12-bit resolution. Force feedback via the analog conversion is used to both monitor fault forces generated during a jam condition within the system and to provide quality information of the force required to destructively tear an envelope during testing. The printed circuit board contains several output channels, with each isolated and buffered through a dry-contact electro-mechanical relay. One output is dedicated to operating an armature-type electromechanical solenoid integrated into the measurement testing assembly and derives its power from the 36-volt DC motor drive power supply. Further, motion homing or zeroing limit switches are mounted so that each axis of motion of the testing device may be moved to a pre-determined end point.

The second section 12 of the housing houses the envelope testing mechanisms. An envelope is inserted through opening 15 and placed in contact with the desired testing mechanism to facilitate testing. Various testing modules may be included within the housing. Among those testing modules are mechanisms to test adhesive thickness, envelope burst strength and graphic content quality.

Figure 3:
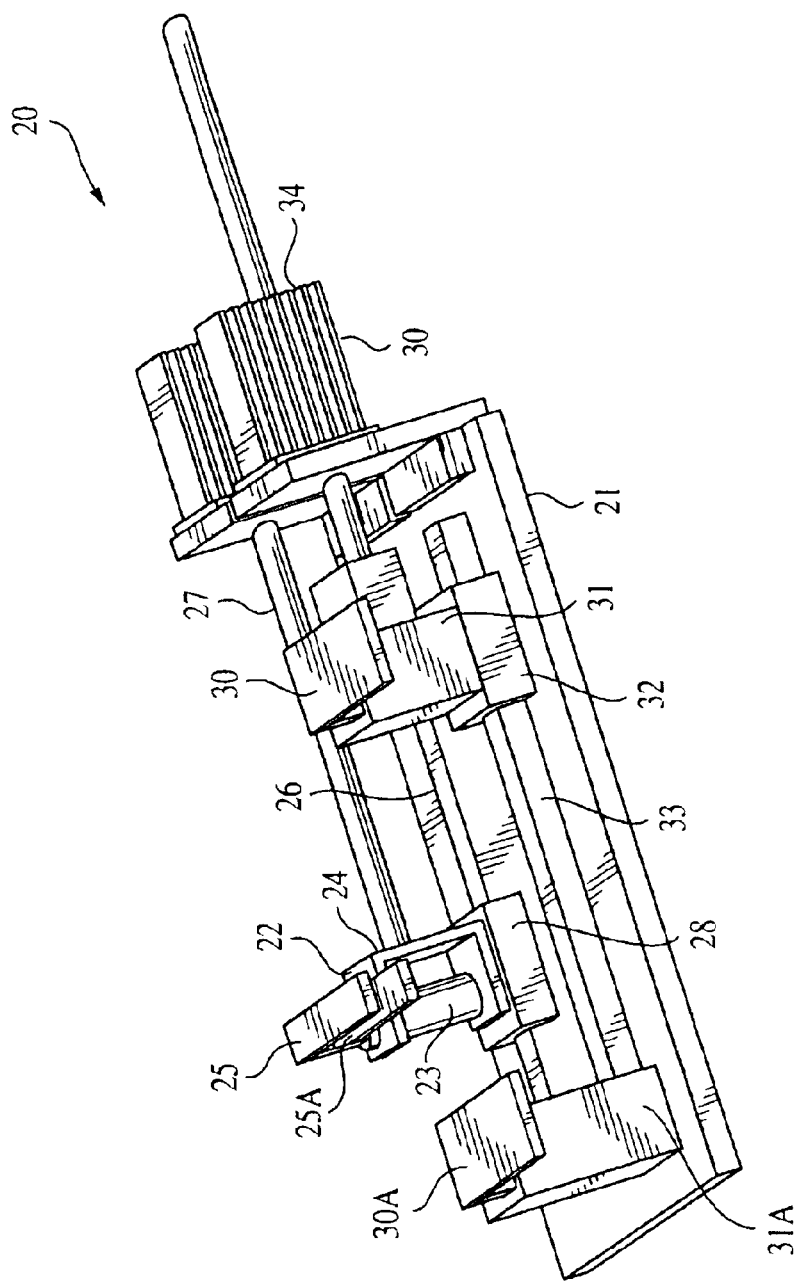
FIG. 3 is a perspective view of the testing mechanism of the envelope-testing unit.

FIG. 3 illustrates testing mechanism 20 that is utilized to test both the burst strength of the envelope and the thickness of the adhesive on the envelope's seal. Testing mechanism 20 comprises base 21 upon which any desired specific testing devices are mounted. Base 21 is preferably constructed of an aluminum alloy and contains keyed slots to allow for the placement of precision ball bearing linear slides and mount points for linear actuators. Adhesive thickness testing micrometer 22 comprises rotary actuator 23 mounted in on angle bracket 24. Angle bracket 24 is mounted on tine slide block 28 that allows lateral movement of the entire unit. Tines 25 and 25A of the micrometer are mounted in tine blocks (not illustrated) and are movable in a vertical manner to allow for the measurement of an item, such as an envelope, placed within the tines. Preferably, the tines are removable so that the testing device may be utilized for a multitude of applications, including varying sizes and types of envelopes. The entire micrometer is laterally movable along rail 26. Thrust for the movement of the micrometer is provided by the turning of an internal rotator nut that is in communication with the actuator. In use, the adhesive seal portion of an envelope is placed between tines 25 and 25A and the tines are positioned so that they are in contact with the adhesive. At this point a measurement is made and transmitted to the central processing unit via transmission means 27 for evaluation and recordation. Following an initial measurement, the entire micrometer unit moves laterally along rail 26 to a different location on the envelope seal and repeats the measurement process. The measurement process may be repeated at as many locations along the envelope seal as is desired.

The testing mechanism may also comprise a unit for measuring the side seam strength of an envelope. The side seam strength-testing unit comprises tines 30 and 30A mounted on supports 31 and 31A. Support 31A is fixedly mounted on base 21 while support 31 is mounted on slide block 32. Slide block 32 is positioned so that it may move laterally along rail 33. Actuator 34 provides the power for the lateral movement During usage, an envelope is placed so that tines 30 and 30A are inside the envelope, with each tine adjacent to an opposite end of the envelope. Slide block 32 is moved laterally in a direction away from support 31 and tine 30. Slide block 32 is moved until it breaks the seal on its end of the envelope. At this point, a measurement of the force required to break the seal is transmitted to the central processing unit.

In a preferred embodiment of the testing system, a visual testing means may also be incorporated into the system. The visual testing means may include a camera that visually observes envelopes placed within the system and monitors the quality of the graphics on the envelope. This is accomplished via the incorporation of a digital camera in the system that compares the envelope being tested with a stored image of an acceptable envelope. Preferably, a high-resolution black and white camera is utilized with a fire-wire interface. Any colors in the graphics may be monitored via the addition of a precision set of subtractive primary filters and a filter free position that is mounted on a disk. The filter free disk is rotated in front of the camera lens to separate individual primary colors into discrete black and white images. The resulting images will be spliced into the existing post processing module to produce four separate frames per envelope and facilitating cross correlation between the frames. Further, an ultraviolet light source may be utilized to determine the presence of UV dye in the adhesive of the envelope. The use of the UV light allows for a visual inspection of adhesive presence where it is not desired and along the seams of a window in the envelope.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

We claim:

1. A device for testing envelopes comprising:
   a) a housing;
   b) a video display unit;
   c) a central processing unit capable of receiving and storing data;
   d) a mechanism for testing an amount of adhesive on the seal of an envelope; and
   e) a mechanism for testing the force required to break a seam on the envelope.

2. The device of claim 1, wherein the mechanism for testing an amount of adhesive and the mechanism for testing the force required to break a seam are in electronic communication with the central processing unit such that data generated from the mechanisms for testing is transmitted to the central processing unit.

3. The device of claim 1, wherein the video display unit comprises a touch screen video display unit.

4. The device of claim 1, wherein the mechanism for testing an amount of adhesive comprises a plurality of tines that are vertically movably so as to determine the thickness of an amount of adhesive.

5. The device of claim 4, wherein the mechanism for testing an amount of adhesive is laterally movable so as to allow testing of an amount of adhesive at a plurality of positions along the envelope.

6. The device of claim 1, wherein the mechanism for testing the force required to break a seam of an envelope comprises a plurality of tines and wherein at least one of the tines is laterally movable.

7. The device of claim 6, wherein the mechanism for testing the force required to break the seam of an envelope comprises first and second tines and wherein the first tine is in a fixed position and the second tine is laterally movable away in a direction away from the first tine.

8. The device of claim 1, wherein the device further comprises a means for testing the quality of graphics printed on the envelope.

9. The device of claim 8, wherein the means for testing the quality of graphics comprises a digital imaging camera that is in electronic communication with the central processing unit such that data generated from the digital imaging camera is transmitted to the central processing unit.

10. The device of claim 9, wherein the means for testing the quality of the graphics includes a means for testing presence and quality of color on the envelope.

11. The device of claim 1, wherein the device further comprises an ultraviolet light to allow for manual visual testing of the envelope.

* * * * *